(12) United States Patent
Belford et al.

(10) Patent No.: US 8,692,190 B2
(45) Date of Patent: *Apr. 8, 2014

(54) FAIMS HAVING A DISPLACEABLE ELECTRODE FOR ON/OFF OPERATION

(75) Inventors: Michael W. Belford, Los Altos, CA (US); Jean-Jacques Dunyach, San Jose, CA (US); Mark E. Hardman, Santa Clara, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/429,311

(22) Filed: Mar. 23, 2012

(65) Prior Publication Data

US 2012/0181424 A1    Jul. 19, 2012

Related U.S. Application Data

(63) Continuation of application No. 12/762,176, filed on Apr. 16, 2010, now Pat. No. 8,158,932.

(51) Int. Cl.
*B01D 59/44* (2006.01)
*H01J 49/42* (2006.01)

(52) U.S. Cl.
USPC .......................................... 250/287; 250/281

(58) Field of Classification Search
USPC ......... 250/280, 281, 282, 287, 288, 289, 290, 250/291, 292
See application file for complete search history.

(56) References Cited

U.S. PATENT DOCUMENTS

| | | | |
|---|---|---|---|
| 5,719,392 A | 2/1998 | Franzen | |
| 6,744,043 B2 | 6/2004 | Loboda | |
| 6,753,522 B2 | 6/2004 | Guevremont et al. | |
| 7,223,971 B2 | 5/2007 | Guevremont et al. | |
| 7,399,961 B2 | 7/2008 | Chen et al. | |
| 7,417,225 B2 | 8/2008 | Guevremont et al. | |
| 7,777,180 B2 | 8/2010 | Hill, Jr. et al. | |
| 8,049,167 B2 * | 11/2011 | Rorrer et al. | 250/286 |
| 8,158,932 B2 * | 4/2012 | Belford et al. | 250/287 |
| 2003/0089849 A1 | 5/2003 | Guevremont et al. | |
| 2003/0106996 A1 | 6/2003 | Covey et al. | |
| 2003/0230711 A1 | 12/2003 | Guevremont et al. | |
| 2004/0094704 A1 | 5/2004 | Miller et al. | |
| 2004/0232326 A1 | 11/2004 | Guevremont et al. | |
| 2005/0139762 A1 | 6/2005 | Miller et al. | |
| 2005/0151072 A1 | 7/2005 | Guevremont et al. | |
| 2005/0156107 A1 | 7/2005 | Miller et al. | |
| 2005/0167587 A1 | 8/2005 | Guevremont et al. | |

(Continued)

*Primary Examiner* — Phillip A Johnston
*Assistant Examiner* — Brooke Purinton
(74) *Attorney, Agent, or Firm* — Thomas F. Cooney

(57) ABSTRACT

A system for analyzing ions comprises: an ion source; a FAIMS cell comprising: (a) a gas inlet; (b) an outer electrode having a generally concave inner surface and comprising: (i) an ion inlet operable to receive the ions from the ion source and a carrier gas from the gas inlet; and (ii) an ion outlet; and (c) an inner electrode having a conduit therethrough and having a generally convex outer surface disposed in a spaced-apart and facing arrangement relative to the inner surface of the outer electrode defining at least one annular on separation region therebetween; and a mass analyzer for mass analyzing ions transmitted by the FAIMS cell through the ion outlet, wherein the inner electrode is moveable between a first position and a second position, the first and second positions facilitating movement of the ions through the at least one annular ion separation region and the conduit, respectively.

11 Claims, 14 Drawing Sheets

(56) References Cited

U.S. PATENT DOCUMENTS

| | | |
|---|---|---|
| 2005/0178962 A1 | 8/2005 | Guevremont et al. |
| 2005/0178964 A1 | 8/2005 | Guevremont et al. |
| 2005/0194527 A1* | 9/2005 | Guevremont et al. ........ 250/285 |
| 2005/0194532 A1 | 9/2005 | Guevremont et al. |
| 2005/0218320 A1 | 10/2005 | Guevremont et al. |
| 2006/0038121 A1 | 2/2006 | Guevremont |
| 2006/0060773 A1 | 3/2006 | Guevremont et al. |
| 2006/0124848 A1 | 6/2006 | Wynn |
| 2006/0151694 A1 | 7/2006 | Guevremont et al. |
| 2006/0255264 A1 | 11/2006 | Belford |
| 2006/0289745 A1 | 12/2006 | Miller et al. |
| 2007/0069120 A1 | 3/2007 | Shvartsburg et al. |
| 2007/0158543 A1 | 7/2007 | Clowers et al. |
| 2007/0176092 A1 | 8/2007 | Miller et al. |
| 2007/0200059 A1 | 8/2007 | Tang et al. |
| 2007/0228269 A1 | 10/2007 | Miller et al. |
| 2007/0252082 A1 | 11/2007 | Miller et al. |
| 2008/0067366 A1 | 3/2008 | Belford |
| 2008/0128609 A1 | 6/2008 | Miller et al. |
| 2008/0156978 A1 | 7/2008 | Shvartsburg et al. |
| 2008/0251714 A1 | 10/2008 | Juan et al. |
| 2009/0014641 A1 | 1/2009 | Bateman et al. |
| 2009/0090853 A1 | 4/2009 | Schoen et al. |
| 2009/0101812 A1 | 4/2009 | Thomson |
| 2009/0134322 A1 | 5/2009 | Thomson |
| 2009/0166526 A1 | 7/2009 | Nuutinmaeki |
| 2009/0294648 A1 | 12/2009 | Schneider et al. |
| 2009/0294650 A1 | 12/2009 | Schneider et al. |

* cited by examiner

FAIMS HAVING A DISPLACEABLE ELECTRODE FOR ON/OFF OPERATION

CROSS REFERENCE TO RELATED APPLICATION

This application is a Continuation of and makes claim, under 35 U.S.C. 120, to the right of priority to and the benefit of the filing date of co-pending U.S. patent application Ser. No. 12/762,176 entitled "FAIMS having a Displaceable Electrode for On/Off Operation" which was filed on Apr. 16, 2010 and applied for in the names of the Applicants of the instant application and assigned to the assignee of the instant application, said co-pending application hereby incorporated by reference herein in its entirety.

FIELD OF THE INVENTION

The present invention relates generally to ion spectrometry, and more particularly to coupling between an ion mobility spectrometry device, such as a high field asymmetric ion mobility spectrometry (FAIMS) cell, and a mass spectrometer.

BACKGROUND OF THE INVENTION

In ion mobility spectrometry devices, separation of gas-phase ions is accomplished by exploiting variations in ion drift velocities under an applied electric field arising from differences in ion mobilities. One well-known type of ion mobility spectrometry device is the High Field Asymmetric Waveform Ion Mobility Spectrometry (FAIMS) cell, also known by the term Differential Ion Mobility Spectrometry (DIMS) cell, which separates ions on the basis of a difference in the mobility of an ion at high field strength (commonly denoted as $K_h$) relative to the mobility of the ion at low field strength (commonly denoted as K). Briefly described, a FAIMS cell consists of a pair of spaced apart electrodes that define therebetween a separation region through which a stream of ions is directed. An asymmetric waveform comprising a high voltage component and a lower voltage component of opposite polarity, together with a DC voltage (referred to as the compensation voltage, or CV) is applied to one of the electrodes. When the ion stream contains several species of ions, only one ion species is selectively transmitted through the FAIMS cell for a given combination of asymmetric waveform peak voltage (referred to as the dispersion voltage, or DV) and CV. The remaining species of ions drift toward one of the electrode surfaces and are neutralized. The FAIMS may be operated in single ion detection mode, wherein the DV and CV are maintained at constant values, or alternatively the applied CV may be scanned with time to sequentially transmit ion species having different mobilities.

FAIMS cells may be used for a variety of purposes, including providing separation or filtering of an ion stream prior to entry into a mass analyzer. An example of this type of application is disclosed in U.S. Pat. No. 6,822,224 to Guevremont. When a FAIMS apparatus is used in isolation, the identity of the peaks appearing in FAIMS CV spectra can not always be unambiguously confirmed due to the unpredictable changes in $K_h$ at high electric fields. One way to extend the capability of instruments based on the FAIMS concept is to provide a way to determine the make-up of the FAIMS CV spectra more accurately, for example, by introducing ions from the FAIMS device into a mass spectrometer for mass-to-charge (m/z) analysis. Likewise, use of a FAIMS apparatus to separate ionic species prior to their introduction into a mass spectrometer can enhance the resulting mass spectrum by eliminating noise-producing background ions as well as by enabling the separate detection of some ionic species, such as isomers, that have identical mass-to-charge ratios.

Unfortunately, sequential use of a FAIMS spectrometer and a mass spectrometer in the fashion described above can lead to poor detected signal intensity, since the percentage transmission through the combined apparatus will be the product of the separate transmission percentages through each of the FAIMS and MS devices. Thus, in those cases in which a mass spectrometer alone may provide adequate analytical capabilities, it is often necessary to remove all or a portion of a front-end FAIMS apparatus to obtain the best results. Further, differing methods of interfacing to ion sources may necessitate replacement of one ion source for another at the same time that the FAIMS apparatus is removed. For instance, in some conventional FAIMS-MS hybrid systems, the FAIMS electrode set must be removed from the mass spectrometer and replaced with a standard ion source housing in order to pass all ions into the MS instrument. This takes a few minutes to accomplish and requires the operator to be present to manually remove the source.

Further, whereas mass spectrometers generally operate under high vacuum conditions, FAIMS analyzers operate at atmospheric or near-atmospheric pressure, since the differential mobility that is exploited is caused by interactions of ions with an inert molecular bath gas, typically containing helium. The gas or gases supplied to the FAIMS analyzer typically provide the additional functions of sweeping or carrying the ions through the apparatus and de-solvating charged liquid droplets. The carrier gas portion, after sweeping ions through the FAIMS apparatus from an ion inlet to an ion outlet, must be subsequently substantially vented to atmosphere so as to not interfere with the evacuated environment of the mass spectrometer. The de-solvating gas portion typically flows outward through the FAIMS ion inlet in counter flow to the movement of ions. Such configurations can lead to undesirably high consumption of helium or other inert gases. Also, the counter current gas flowing out of the entrance can lead to difficulties in coupling to certain ion sources, such as nano-electrospray sources. Further, operation with negative ion Atmospheric Pressure Chemical Ionization (APCI) sources is not possible due to arcing that occurs when too much helium is introduced into the FAIMS gas mixture. Still further, FAIMS operation at too high pressure (e.g., near-atmospheric pressure) can lead to too-long residence times within the FAIMS apparatus that interfere with mass spectrometer operation.

Accordingly, there are needs in the art for a FAIMS apparatus that does not require separation from a mass spectrometer in order to pass a substantial fraction of ions from an ion source into a mass spectrometer, for FAIMS apparatus having reduced gas consumption, easier coupling to nano-electroospray and APCI ion sources (especially APCI sources operated in negative ion mode), reduced ion residence time, and better integration with mass spectrometers. The present invention addresses such needs.

SUMMARY

The present teachings address, in part, the above-identified needs in the art by providing a displaceable inner electrode that operates as a FAIMS electrode in a first position and as an ion transfer tube in a second position without requiring removal of the FAIMS source from the mass spectrometer. A system for analyzing ions in accordance with the present teachings allows switching between FAIMS separation mode and ion transmission mode using a single set of electrodes. In some embodiments of systems in accordance with the present teachings, a inner electrode of the FAIMS apparatus comprises a cylinder, sphere or ovoid shape that presents a solid surface area when in position for FAIMS separation but that provides, upon rotation or other movement of the electrode into a transmission position, a conduit (a hole or bore) passing through the center of the inner electrode that enables direct transmission of ions from an ion inlet to an ion outlet of the FAIMS. In some embodiments in accordance with the present teachings, reconfiguration of the electrode from the first (FAIMS) position to the second (transmission) position may be accomplished by rotating the electrode on a screw mechanism thereby causing the electrode to both rotate and move laterally.

In a first aspect of the present teachings, a system for analyzing ions is provided, the system comprising: an ion source for generating ions; a High Field Asymmetric Waveform Ion Mobility Spectrometry (FAIMS) cell comprising: (a) a gas inlet; (b) an outer electrode having a generally concave inner surface, the outer electrode comprising: (i) an ion inlet operable to receive the ions from the ion source and a carrier gas from the gas inlet; and (ii) an ion outlet; and (c) an inner electrode having a conduit therethrough and having a generally convex outer surface that is disposed in a spaced-apart and facing arrangement relative to the inner surface of the outer electrode for defining an ion separation region therebetween; and a mass analyzer for mass analyzing ions transmitted by the FAIMS cell through the ion outlet, wherein the inner electrode is moveable between a first position and a second position, the first position facilitating movement of the ions through the ion separation region, the second position facilitating movement of the ions through the conduit.

In another aspect of the present teachings, a system for analyzing ions is provided, the system comprising: an ionization chamber; an atmospheric pressure ion source within the ionization chamber for generating ions; a first reduced pressure chamber; an ion transfer tube having a first end disposed within the ionization chamber for receiving ions from the ion source and a second end disposed within the first reduced pressure chamber; a heater in thermal contact with the ion transfer tube; a carrier gas conduit for introducing a flow of carrier gas into the ion transfer tube; a High Field Asymmetric Waveform Ion Mobility Spectrometry (FAIMS) cell comprising: (a) an outer electrode having a generally concave inner surface, the outer electrode comprising: (i) an ion inlet operable to receive the ions and the carrier gas from the second end of the ion transfer tube; and (ii) an ion outlet; and (b) an inner electrode having a conduit therethrough and having a generally convex outer surface that is disposed in a spaced-apart and facing arrangement relative to the inner surface of the outer electrode for defining an ion separation region therebetween; a mass analyzer for mass analyzing ions transmitted by the FAIMS cell through the ion outlet; and a housing of the mass analyzer comprising at least one evacuated chamber fluidically coupled to the ion outlet of the FAIMS cell, wherein the inner electrode is moveable between a first position and a second position, the first position facilitating movement of the ions through the ion separation region, the second position facilitating movement of the ions through the conduit.

In yet another aspect of the present teachings, a system for analyzing ions is provided, the system comprising: an ion source for generating ions; a High Field Asymmetric Waveform Ion Mobility Spectrometry (FAIMS) cell comprising: (a) a gas inlet; (b) an outer electrode having a generally concave inner surface, the outer electrode comprising: (i) an ion inlet operable to receive the ions from the ion source and a carrier gas from the gas inlet; and (ii) an ion outlet; and (c) an inner electrode having a generally convex outer surface that is disposed in a spaced-apart and facing arrangement relative to the inner surface of the outer electrode for defining an ion separation region therebetween; a mass analyzer for mass analyzing ions transmitted by the FAIMS cell through the ion outlet, the mass analyzer separated from the FAIMS cell by a gap therebetween; a gas-tight coupling between the FAIMS cell and the mass analyzer within the gap; and at least one vacuum port coupled to the mass analyzer for maintaining the mass analyzer and the FAIMS ion separation region at sub-atmospheric pressure.

DETAILED DESCRIPTION OF EMBODIMENTS

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-8, taken in conjunction with the following description.

Prior attempts at transmitting all ions through a FAIMS device include turning off the voltages on the FAIMS electrode and removing the inner electrode altogether. Although these techniques allow ions across the entire m/z range to be transmitted, they are associated with major losses in transmission efficiency.

Figure 1A:
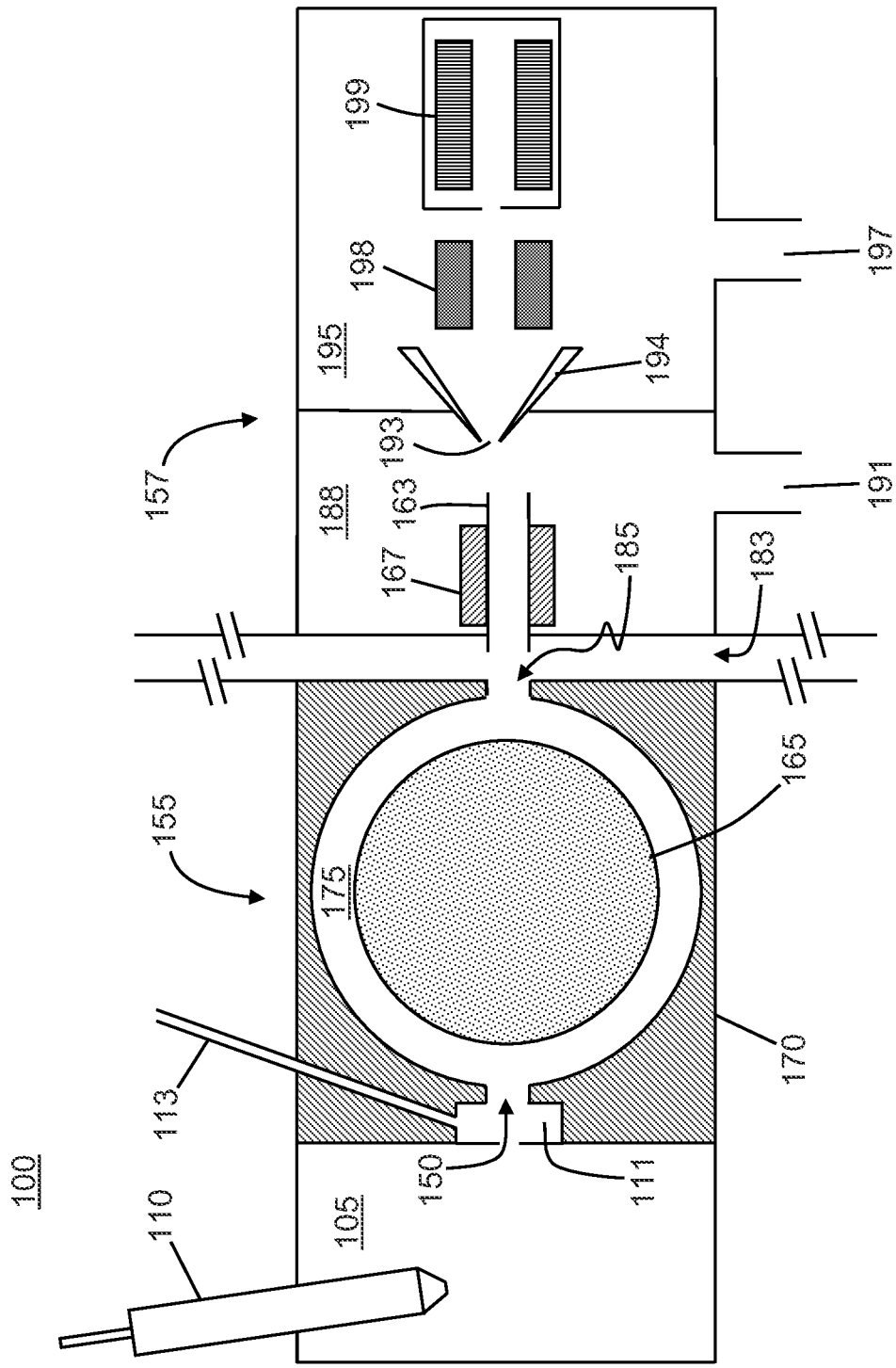
FIG. 1A is a schematic diagram depicting a first known system for analyzing ions including an ion mobility device.

FIG. 1A schematically depicts a first known system 100 for analyzing ions that includes a FAIMS device 155. A solution of sample to be analyzed is introduced as a spray of droplets into an ionization chamber 105 via atmospheric pressure ion source 110. Ionization chamber 105 is maintained at a high pressure relative to the regions downstream in the ion path, typically at or near atmospheric pressure. Atmospheric pressure ion source 110 may be configured as an electrospray ionization (ESI) probe, wherein a high DC voltage (either positive or negative) is applied to the capillary or "needle" through which the sample solution flows. This voltage imparts a charge to the droplets as they are emitted from the capillary exit. The charge accumulates at the droplet surface during solvent evaporation, causing droplet fragmentation and the liberation of analyte ions. Other suitable ionization techniques may be utilized in place of ESI, including without limitation such well-known techniques as atmospheric pressure chemical ionization (APCI), heated electrospray ionization (HESI), and thermospray ionization.

Ions produced by the ion source enter the FAIMS cell 155 through inlet orifice 150 after passing through a desolvation chamber 111. The desolvation chamber is provided with a gas, typically helium or other inert gas, which is introduced into the desolvation chamber 111 via a gas conduit 113. A portion of the gas flows back into the ionization chamber 105 in counter-flow to the ions and droplets and serves to desolvate charged droplets. Another portion of the gas combines with the analyte ions in chamber 111 and serves as a carrier gas through the FAIMS apparatus 155. The combined ion/carrier gas flow then enters FAIMS cell 155 through inlet orifice 150. The carrier gas flow may be carefully metered to maintain flow rates within predetermined limits which will depend on the FAIMS cell size, electrode geometry, and operational considerations.

Generally speaking, the FAIMS cell 155 includes inner and outer electrodes 165 and 170 having radially opposed surfaces, which define therebetween an annular separation region 175 through which the ions are transported. The FAIMS cell geometry depicted in FIG. 1A, as well as in other figures herein may be generally referred to as a "side-to-side FAIMS cell", in which the longitudinal axes (axes of cylindrical surfaces, directed out of the page) of inner electrode 165 and outer electrode 170 are oriented transversely with respect to the overall direction of ion flow. The principles of the design and operation of FAIMS cells and other ion mobility spectrometry devices have been extensively described elsewhere in the art (see, for example, U.S. Pat. No. 6,639,212 to Guevremont et al., incorporated by reference herein in its entirety), and hence will not be described in detail herein. In brief, the carrier gas and ions flow through the separation region 175 from inlet orifice 150 to exit orifice 185. Ion separation is effected within the separation region 175 of the FAIMS cell 155 by applying an asymmetric waveform having a peak voltage DV and a compensation voltage CV to one of the inner or outer electrodes, 165, 170. The values of CV and DV are set to allow transmission of a selected ion species through separation region 175. Other ion species having different relative values of high field and low field mobilities will migrate to the surface of one of the electrodes and be neutralized.

Still referring to FIG. 1A, the selected ions emerge from the FAIMS cell 155 through exit orifice 185 and pass through a small gap 183 separating the FAIMS cell 155 from a mass spectrometer 157. Whereas most of the carrier gas exhausts through the gap 183 at atmospheric pressure, ions are electrostatically guided into at least one reduced pressure chamber 188 of the mass spectrometer 157 through an orifice in the mass spectrometer or through an ion transfer tube 163. The at least one reduced pressure chamber may be evacuated by a vacuum port 191. The ion transfer tube 163 may comprise an elongated tube or capillary that may be formed from a metallic material such as stainless steel. Use of an electrically conductive material allows an offset voltage to be applied to ion transfer tube 163 to develop electric fields that urge ions into and through the ion transfer tube. Alternatively, a non-metallic material such as quartz or glass may be employed to construct ion transfer tube 163. At least a portion of ion transfer tube 163 is surrounded by and in good thermal contact with a heat source, such as heater jacket 167. The heater jacket 167, which may take the form of a conventional resistance heater, is operable to raise the temperature of ion transfer tube 163 to promote further desolvation of droplets entering the ion transfer tube 163.

From the at least one reduced pressure chamber 188, ions are transferred through an orifice 193 of a skimmer 194 into a high vacuum chamber 195 maintained at a low pressure (typically around 100 millitorr) relative to the reduced pressure chamber 188. The high vacuum chamber 195 is typically evacuated by turbo or similar high-vacuum pumps via a vacuum port 197. The skimmer 194 may be fabricated from an electrically conductive material, and an offset voltage may be applied to skimmer 194 to assist in the transport of ions through interface region and into skimmer orifice 193. Ions passing through skimmer orifice 193 may be focused or guided through ion optical assembly 198, which may include various electrodes forming ion lenses, ion guides, ion gates, quadrupole or octopole rod sets, etc. The ion optical assembly 198 may serve to transport ions to an analyzer 199 for mass analysis. Analyzer 199 may be implemented as any one or a combination of conventional mass analyzers, including (without limitation) a quadrupole mass analyzer, ion trap, or time-of-flight analyzer.

Figure 1B:
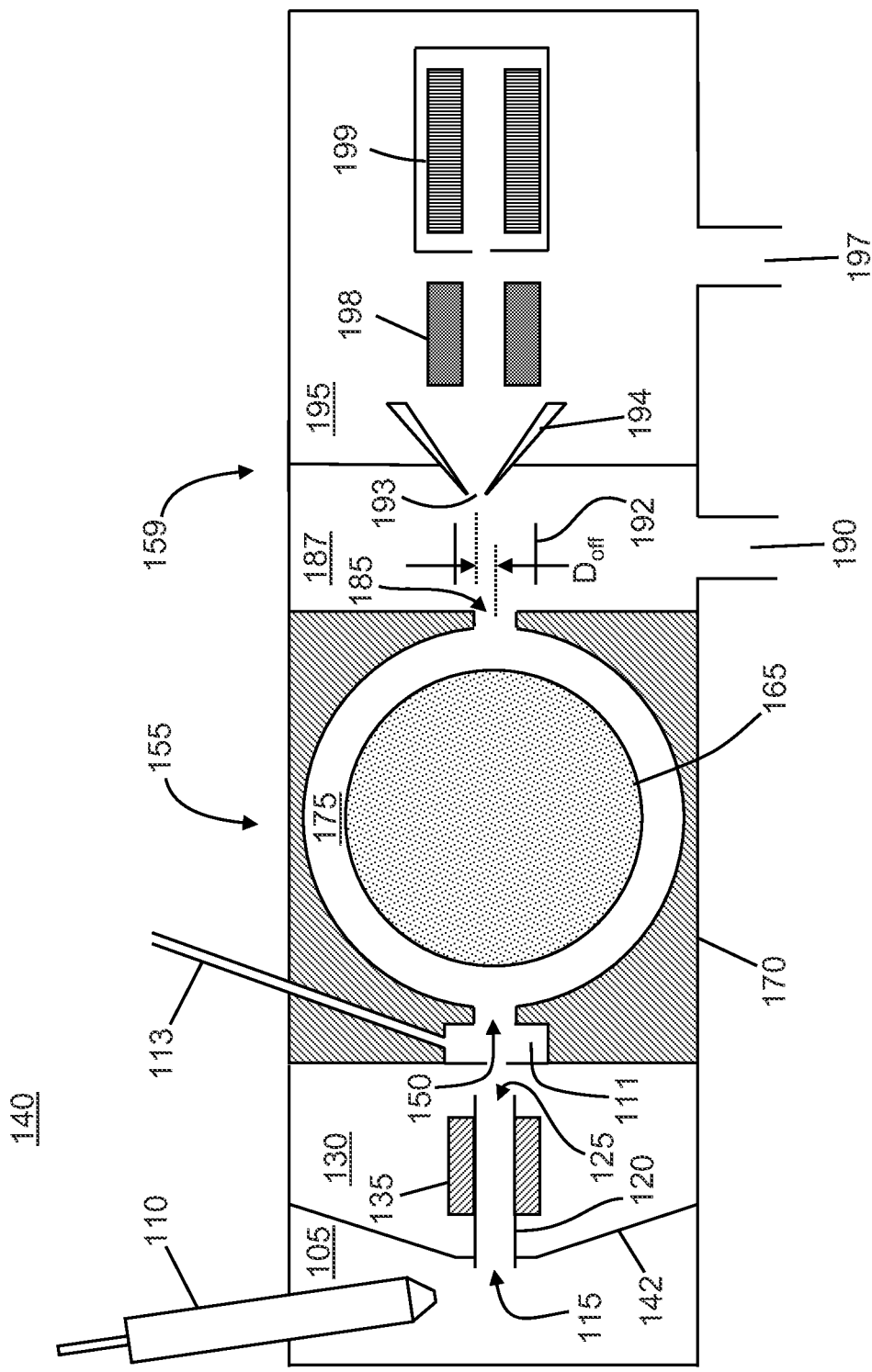
FIG. 1B is a schematic diagram depicting a second known system for analyzing ions including an ion mobility device.

FIG. 1B schematically depicts a second known system 140 for analyzing ions that includes a FAIMS device 155. The components of the FAIMS device 155, ionization chamber 105, atmospheric pressure ion source 110 and mass spectrometer high vacuum chamber 195 shown in FIG. 1B are as described above with reference to FIG. 1A. However, the system 140 includes a direct gas-tight coupling between the FAIMS cell and the mass analyzer portion as well as an additional reduced pressure chamber 130 disposed between the ionization chamber 105 and the FAIMS 155. A partition 142 separates the ionization chamber from the reduced pressure chamber 130. The mass spectrometer 159 of the system 140 includes a reduced pressure chamber 187 that is directly coupled to the outlet orifice 185 of the FAIMS 155. Since, in the system 140, the exit orifice 185 is directly coupled to the chamber 187 that is coupled to a vacuum system (via a vacuum port 190), the pressure within the FAIMS cell may itself be sub-atmospheric.

In the system 140 (FIG. 1B), at least a portion of the analyte ions produced in ionization chamber 105 are drawn into the reduced pressure chamber 130 by means of an ion transfer tube 120 that passes through the partition 142. The ion transfer tube 120 comprises an inlet orifice 115 disposed within the ionization chamber 105 and an outlet orifice 125 disposed within the reduced pressure chamber 130. The ion transfer tube 120 is an elongated tube or capillary that may be formed from a metallic material such as stainless steel. Use of an electrically conductive material allows an offset voltage to be applied to the ion transfer tube 120 to develop electric fields that urge ions into and through the ion transfer tube. Alternatively, a non-metallic material such as quartz may be employed to construct the ion transfer tube 120. The reduced-pressure chamber 130 may be maintained at a pressure of approximately 100 torr by a mechanical vacuum pump, although this pressure will vary significantly with changes in operating parameters such as flow rates. At least a portion of the ion transfer tube 120 may be surrounded by and in good thermal contact with a heat source, such as heater jacket 135. The heater jacket 135, which may take the form of a conventional resistance heater, is operable to raise the temperature of the ion transfer tube 120 to promote desolvation of droplets entering the ion transfer tube 120, as described below. The outlet orifice 125 of ion transfer tube 120 is positioned adjacent to the inlet orifice 150 of FAIMS cell 155 such that ions exiting the outlet orifice 125 enter the FAIMS cell 155 through the inlet orifice 150 after passing through the desolvation chamber 111. As stated previously, an inert gas is introduced into the desolvation chamber 111 via a conduit 113 to facilitate desolvation as well as to serve as a carrier gas through the FAIMS cell 155.

Still referring to FIG. 1B, it may be observed that, after passing through the FAIMS cell 155, the selected ions emerge through the exit orifice 185 into the reduced pressure chamber 187. The reduced pressure chamber 187 is evacuated via vacuum port 190 to a pressure of approximately 1 torr, thereby removing a substantial portion of the carrier gas, although this pressure may vary considerably depending on operating parameters and instrument configuration. The ions leaving the FAIMS cell 155 may be focused by tube lens 192 (or other suitable ion optics) and are transferred through the orifice 193 of skimmer 194 into the high vacuum chamber 195 as discussed above. As a safeguard against transport of droplets and/or other condensed phase material into the vacuum chamber 195, which could result in contamination of the mass analyzer 199 and consequent malfunction, the ion flow axis of skimmer orifice 193 may be laterally offset by a certain distance (indicated as $D_{off}$ in FIG. 1B) with respect to the ion flow axes of the exit orifice 185 of the FAIMS cell 155 so that no line-of-sight flight path exists from the FAIMS cell 155 to the analyzer 199. Droplets moving through the reduced pressure chamber 187 are undeflected (or deflected by a lesser degree relative to ions) by the electric field created by the voltages applied to skimmer 194 and/or other conductive surfaces, and will thus impact the solid surfaces of skimmer 194 rather than passing through orifice 193.

Figure 2A:
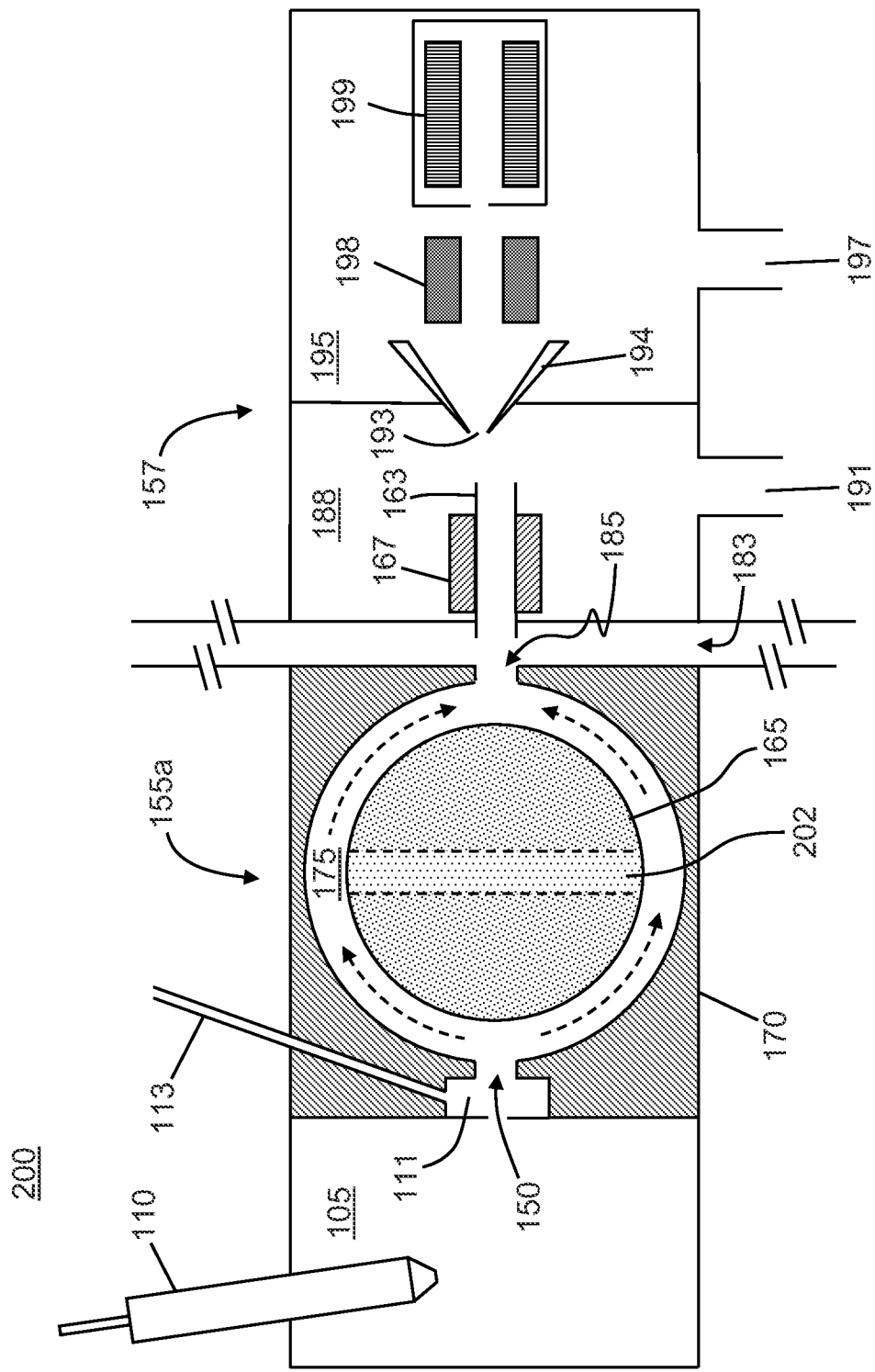
FIG. 2A is a schematic diagram depicting a first embodiment of a system for analyzing ions including an ion mobility device in accordance with the present teachings, wherein the ion mobility device is configured for FAIMS operation.
Figure 2B:
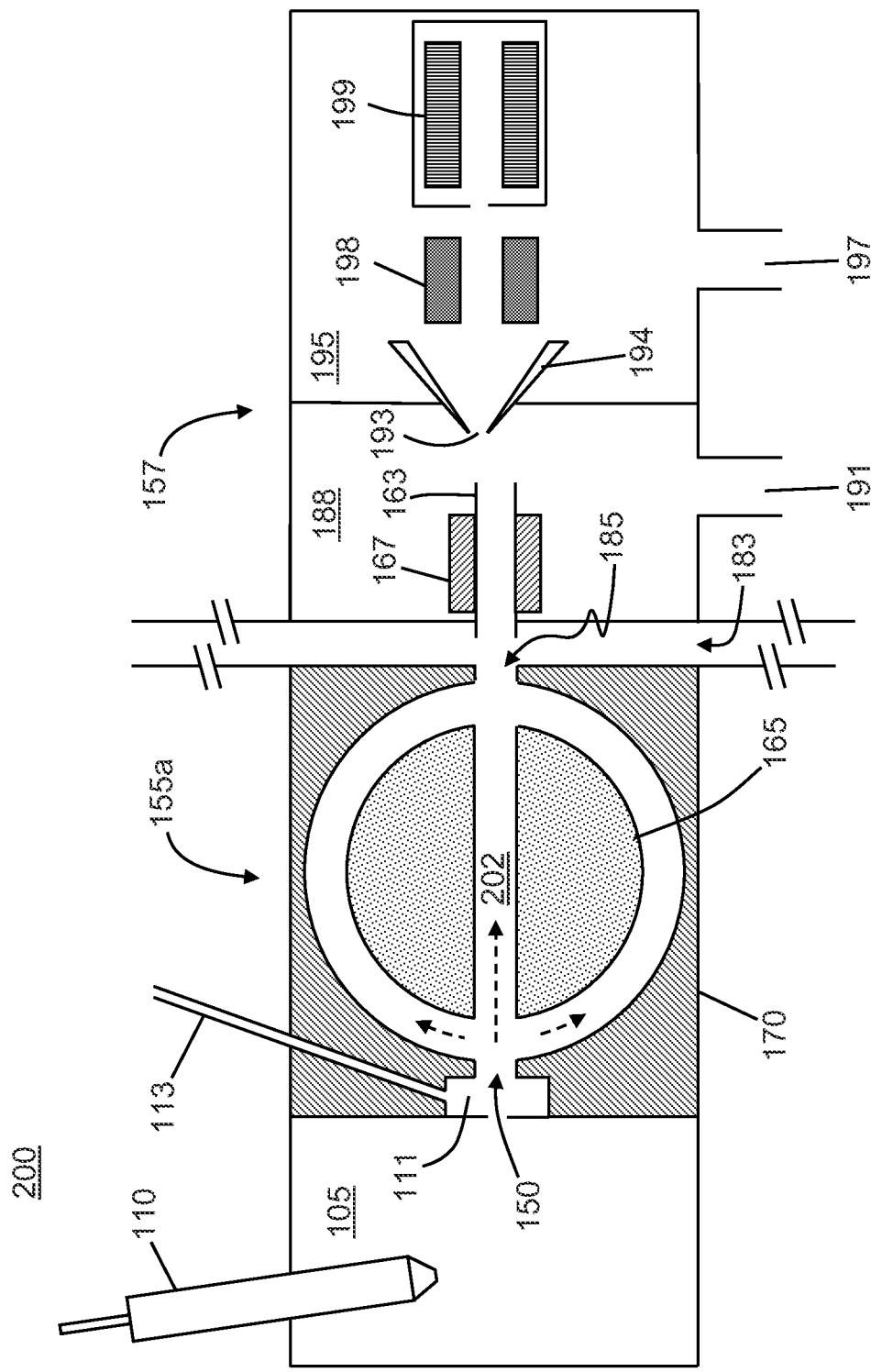
FIG. 2B is a schematic diagram depicting the same system as shown in FIG. 2A, but wherein the ion mobility device is configured to operate as a non-selective ion transport apparatus.

FIGS. 2A-2B are schematic diagrams depicting a first embodiment of a system for analyzing ions including an ion mobility device in accordance with the present teachings. The system 200 (FIGS. 2A-2B) comprises several similar components, numbered similarly, to those already illustrated in and discussed in reference to FIG. 1A. However, in contrast to the system illustrated in FIG. 1A, the system 200 comprises a FAIMS cell 155a that is modified from the apparatus shown in FIG. 1A. In particular, the FAIMS 155a (FIGS. 2A-2B) has a cylindrical inner electrode 165 having a throughgoing conduit (a hole or bore) 202 that is substantially perpendicular to the cylindrical axis (note that the axis of the cylindrical inner electrode 165 is perpendicular to the plane of the drawing in FIG. 2A and other of the accompanying figures). Furthermore, the cylindrical inner electrode 165 is disposed within the FAIMS cell 155a such that it may be rotated about its axis so as to change the disposition or orientation of the conduit 202 with respect to the other system components.

In FIG. 2A, the cylindrical inner electrode is shown in a configuration suitable for FAIMS operation, with the conduit 202 disposed perpendicular to a hypothetical line connecting the inlet orifice 150 to the outlet orifice 185. The flow of carrier gas through the FAIMS is shown by dashed arrows in FIGS. 2A-2B. It is this carrier gas flow that causes ions to have a component of movement through the annular separation region 175 around the outer surface of the inner electrode 165 in the direction from the inlet orifice 150 to the outlet orifice 185. Also, dispersion and compensation voltages (DV and CV) applied to the electrodes 165, 170 produce components of ion motion across the annular separation region, in the usual fashion. When the conduit 202 is disposed as shown in FIG. 2A, there is little or no tendency for gas to flow through the conduit 202, a phenomenon which would perturb FAIMS separation. However, if the conduit positions in FIGS. 2A and 2B are related as by a pure rotation, then some gas flowing circumferentially around the outer surface of the center electrode 165 will encounter the openings in the conduit 202 and the gas-flow streamlines or electric fields may be perturbed. The perturbed electric fields or gas-flow streamlines may, in some instances, influence or perturb ion trajectories through the annular separation region 175 thereby possibly affecting FAIMS separation. A following discussion herein discusses a screw-like movement of the center electrode that prevents significant disruption of the overall gas flow between the inlet orifice 150 to the outlet orifice 185 during FAIMS operation.

FIG. 2B shows the same system 200 illustrated in FIG. 2A, but with the conduit 202 disposed along the hypothetical line connecting the inlet orifice 150 to the outlet orifice 185. In this configuration, the FAIMS 155a may be operated as a simple ion transfer tube between the ionization chamber 105 and the gap 183 the two electrodes 165, 170 may be maintained at a common electrical potential such that the CV and DV are inoperative (the FAIMS is essentially disabled) and the flow of ions through the FAIMS is dominated by the flow of carrier gas. In this configuration ions flow through the FAIMS apparatus without separation according to ion mobility variations and the apparatus behaves as a passive ion transport device having three branches one branch through the conduit 202 through the inner electrode 165, a second branch clockwise through the region 175 between the electrodes and a third branch counterclockwise through the region 175. Most of the gas and ion flow will be taken up by the straight-line or direct flow through the conduit 202 through the inner electrode, as indicated by the lengths of the dashed arrows in FIG. 2B. This effect will be especially true if the conduit diameter is significantly greater then the radial width of the region 175. In this fashion, the FAIMS apparatus 155a can transmit a greater proportion of ions through to the mass spectrometer 157 than would be possible by utilizing a disabled conventional FAIMS 155 (cf., FIG. 1A) and thus, in most circumstances, obviates any need to remove all or a portion of the FAIMS apparatus from the mass spectrometer.

Figure 2C:
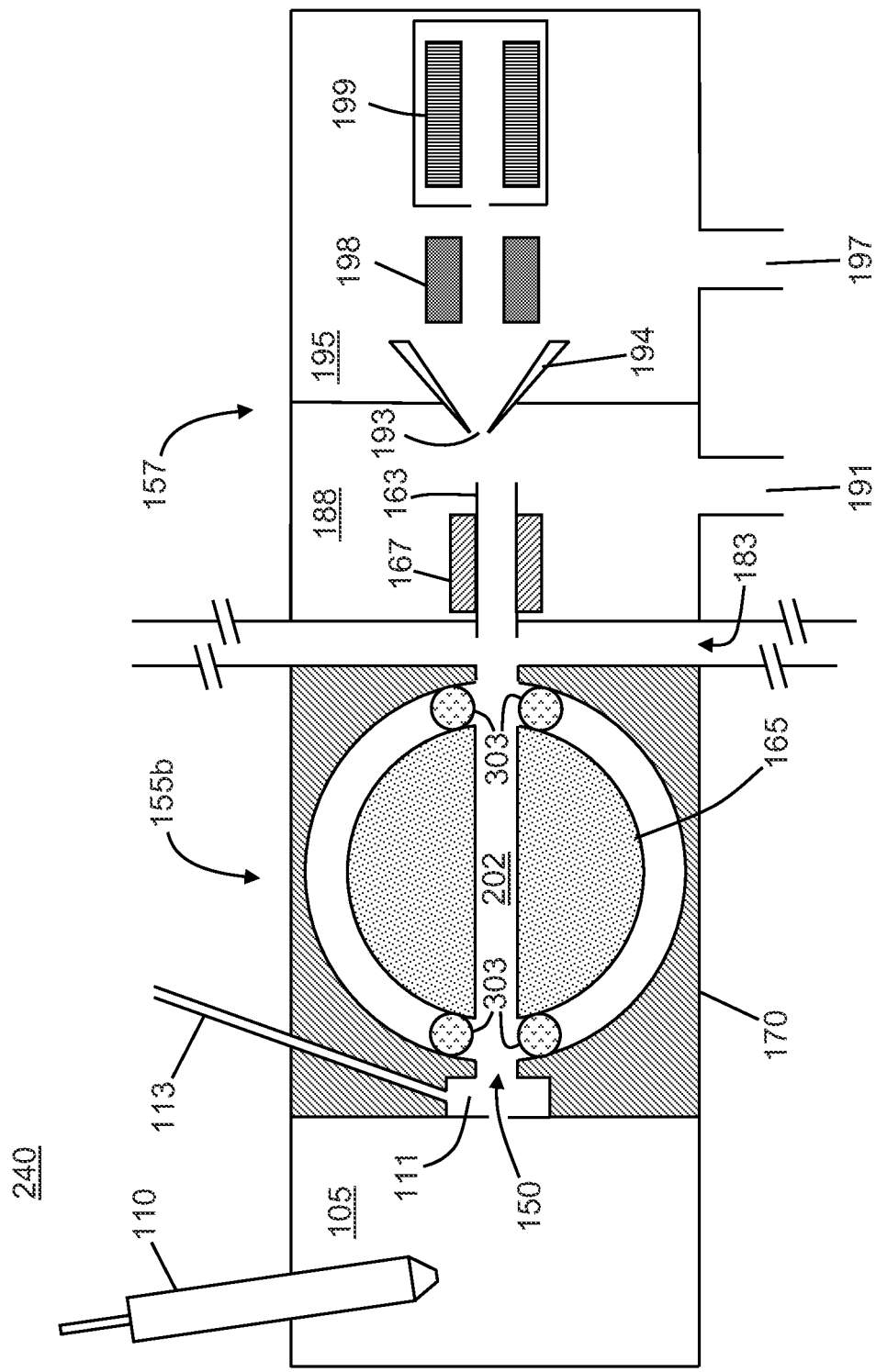
FIG. 2C is a schematic diagram depicting a modification to the system depicted in FIGS. 2A-2B.

FIG. 2C is a schematic diagram depicting another system 240 for analyzing ions comprising a further modified FAIMS cell 155b. In similar fashion to the FAIMS cell 155a (FIGS. 2A-2B), the FAIMS cell 155b (FIG. 2C) comprises a through-going conduit 202 that is substantially perpendicular to the cylindrical axis (perpendicular to the plane of the drawing) of the cylindrical inner electrode 165. Additionally, the FAIMS cell 155b comprises at least one gasket or bushing 303 that either is or may be placed in position so as to block carrier gas flow (and, consequently, ion flow) through the region 175. Advantageously, such gaskets may be placed as close as possible adjacent to the ends of the conduit 202 without blocking the conduit internal area, as shown in FIG. 2C. In this fashion, a seal is created between the conduit 202 and the inlet and exit orifices 150, 185 such that substantially all flow is constrained to flow through the conduit 202 from the inlet orifice 150 to the outlet orifice 185. To create the sealing surface when the inner electrode is rotated into transmission mode, Teflon® bushings (as but one non-limiting example) may be used to form a gas tight seal between the inner electrode and the outer electrode. This will create a continuous transfer tube from the inlet orifice of the FAIMS cell throughout to the outlet orifice. The one or more gaskets or bushings 303 will not hinder the electric fields in FAIMS mode due to their non-conductive properties.

The seated configuration shown in FIG. 2C prevents any spectral broadening that could result as a result of simultaneous ion flow through paths having different lengths (e.g., through the conduit 202 and the region 175) and provides greater transmission efficiency than the configuration shown in FIG. 2B, since ion collisions with the curved surfaces bounding the region 175 are eliminated. Only one electrode configuration is illustrated for the system 240. However, as previously discussed in regard to FIGS. 2A-2B, the inner electrode of the FAIMS 155b may be rotatably configured so as to allow the apparatus 155b to operate in two alternative modes a FAIMS mode and an ion transfer mode.

Figure 3A:
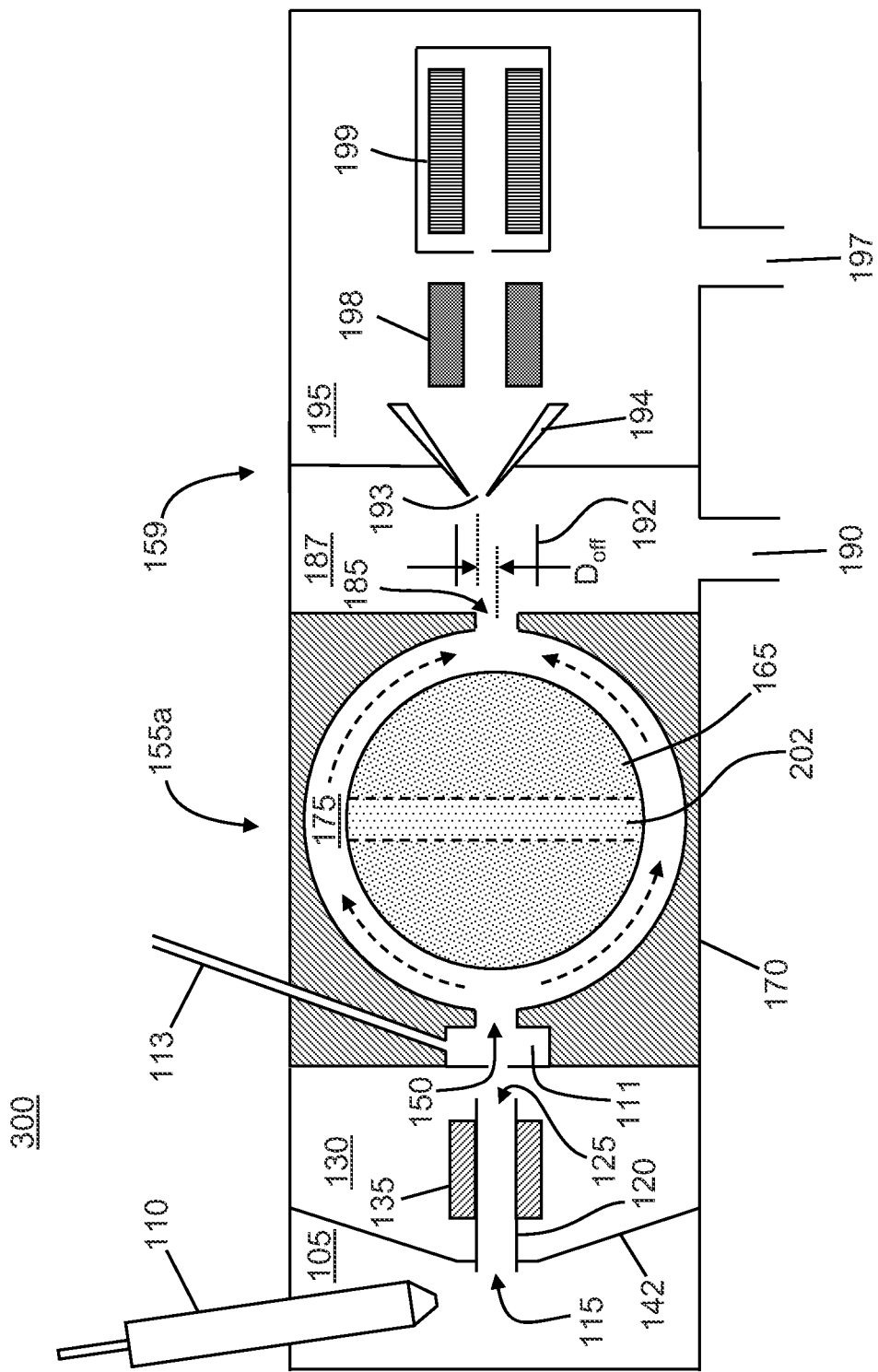
FIG. 3A is a schematic diagram depicting a second embodiment of a system for analyzing ions including an ion mobility device in accordance with the present teachings, wherein the ion mobility device is configured for FAIMS operation.
Figure 3B:
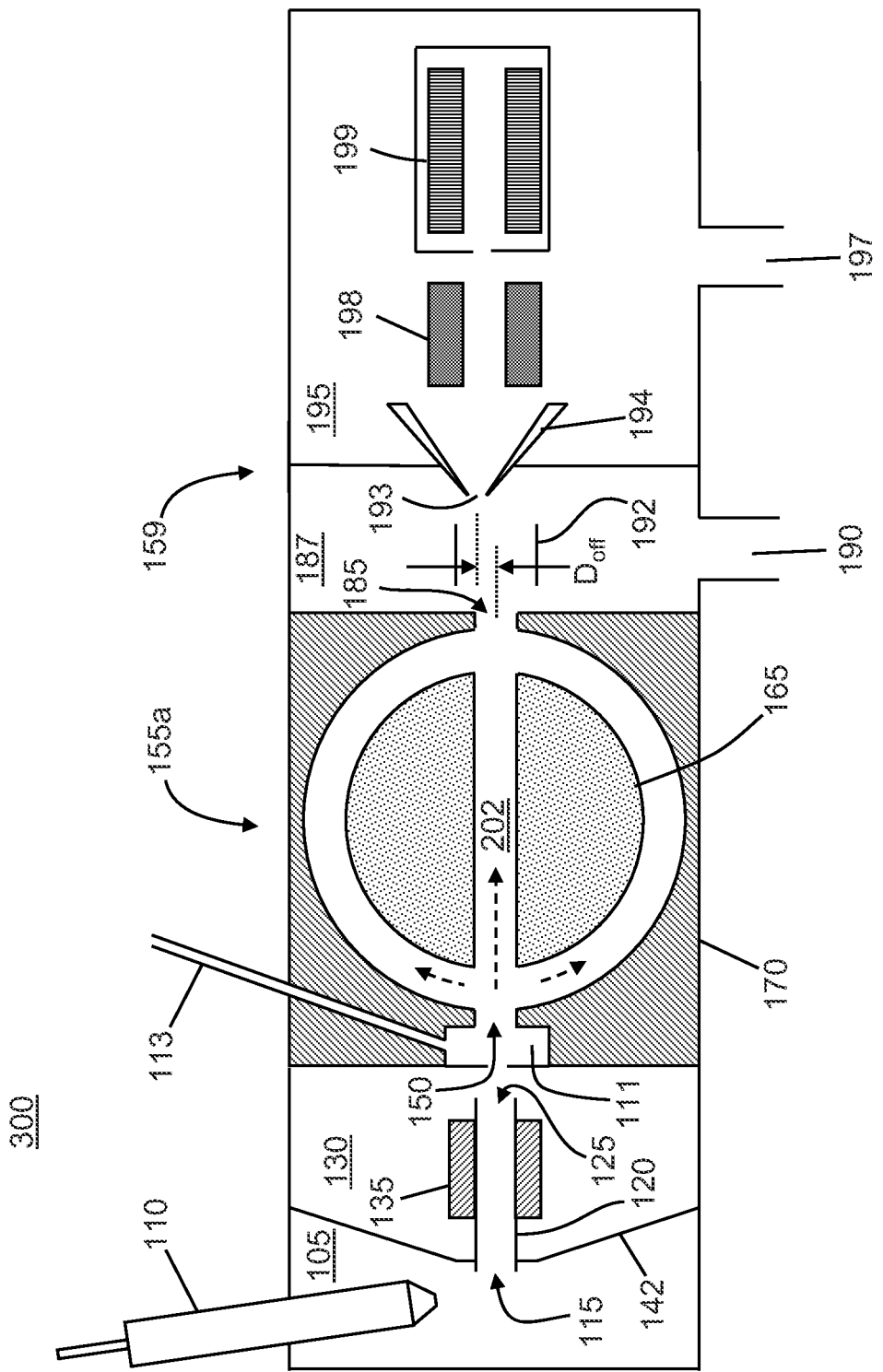
FIG. 3B is a schematic diagram depicting the same system as shown in FIG. 3A, but wherein the ion mobility device is configured to operate as a non-selective ion transport apparatus.
Figure 3C:
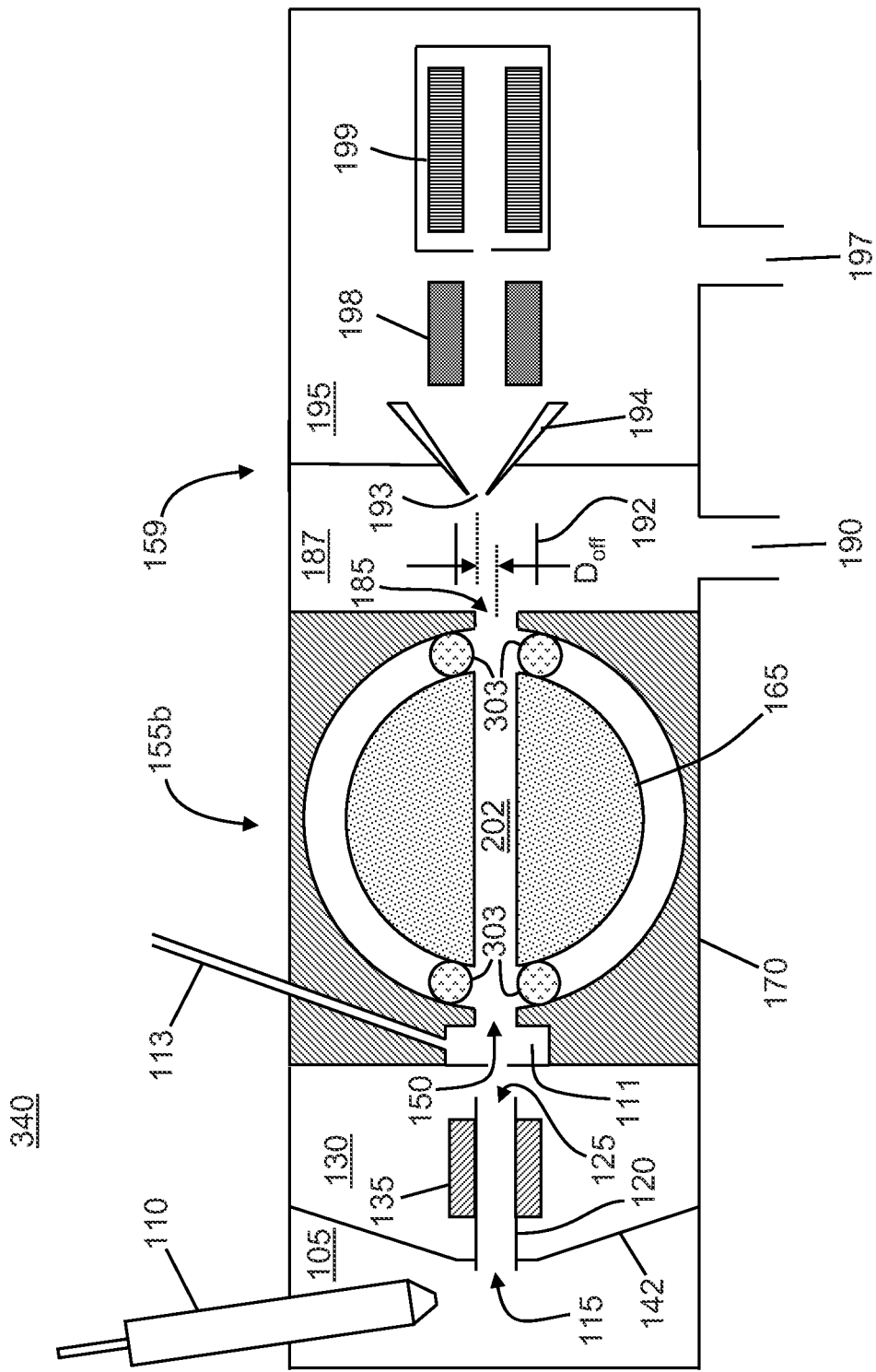
FIG. 3C is a schematic diagram depicting a modification to the system depicted in FIGS. 3A-3B.

FIGS. 3A-3B are schematic diagrams depicting another embodiment of a system for analyzing ions including an ion mobility device in accordance with the present teachings. The system 300 (FIGS. 2A-2B) comprises several similar components, numbered similarly, to those already illustrated in and discussed in reference to FIG. 1B. However, in contrast to the system 140 illustrated in FIG. 1B, the system 200 comprises the FAIMS cell 155a that was described in reference to FIGS. 2A-2B. Thus, as previously discussed in regard to FIGS. 2A-2B, the inner electrode of the FAIMS 155a may be movably configured so as to allow the apparatus 155a to operate in two alternative modes a FAIMS mode and an ion transfer mode. The system 340 shown in FIG. 3C provides a further modification whereby the FAIMS cell 155b, having flow restricted to the central conduit 202 by means of gaskets 303, is employed. Although only one configuration (corresponding to operation in ion transfer mode) is illustrated in FIG. 3C, the inner electrode of the FAIMS 155b may be movably configured so as to allow the apparatus 155b to also operate in the alternative FAIMS mode.

As discussed previously herein, the ability to configure the FAIMS cells shown in FIGS. 3A-3C in an ion transfer mode will, in most circumstances, obviate any need to remove the FAIMS apparatus from the associated mass spectrometer in order to obtain greater throughput. Whereas the FAIMS cells of the systems 200, 240 (FIGS. 2A-2C) operate at atmospheric pressure, the FAIMS cells of the systems 300, 340 (FIGS. 3A-3C) operate at sub-atmospheric pressure. Evacuation to sub-atmospheric pressure is provided by the vacuum port 190 of the reduced pressure chamber 187 and, possibly, by an additional vacuum port (not shown) coupled to the reduced pressure chamber 130. Experimental data obtained by the inventors indicates that the overall ion transfer efficiency of the displaceable inner electrode of the systems 300, 340 (FIG. 3) is, in general, greater than that of corresponding electrode of the systems 200, 240 (FIG. 2). By sealing the FAIMS cell to the mass spectrometer, ions flow through the FAIMS cell faster and none of the FAIMS gas load is lost before entering the mass spectrometer.

Figure 4A:
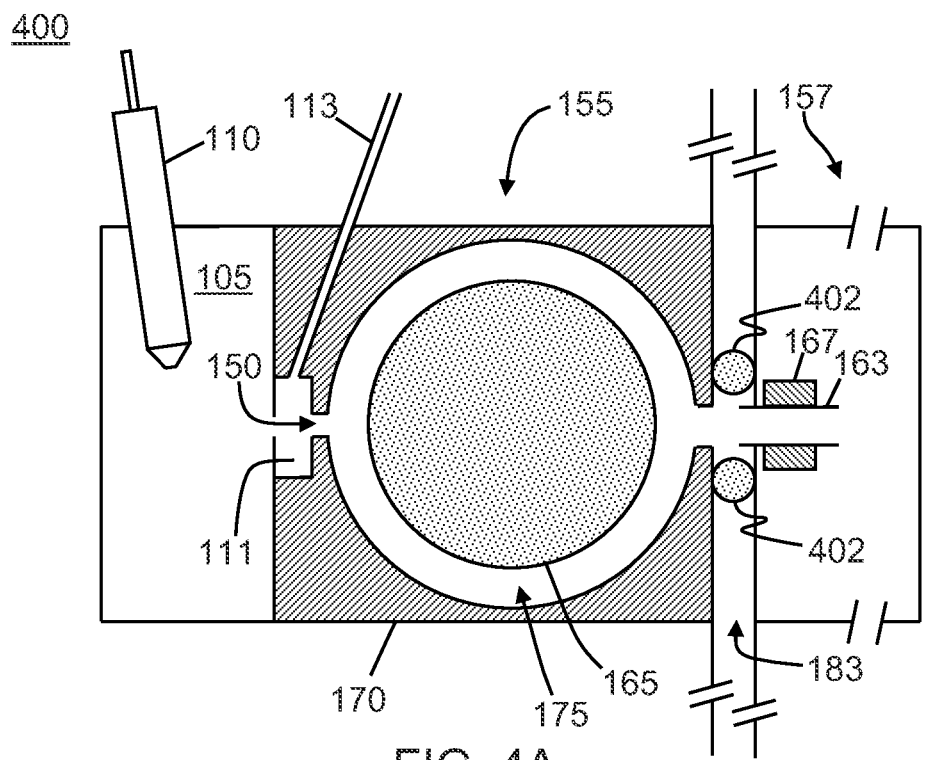
FIG. 4A is a schematic diagram depicting a third embodiment of a system for analyzing ions including an ion mobility device in accordance with the present teachings.

FIG. 4A is a schematic diagram depicting a third embodiment of a system for analyzing ions including an ion mobility device in accordance with the present teachings. The system 400 shown in FIG. 4A is generally similar to the system 100 (FIG. 1A) but with most of the mass spectrometer 157 not illustrated. Accordingly, FIG. 4A employs similar reference numbers for components that have already been introduced in and described in reference to FIG. 1A. As previously described, the system 400 comprises a small gap 183 separating a FAIMS cell 155 from a mass spectrometer 157. However, in contrast to the system 100, carrier gas is not allowed to vent through the gap 183. Instead, in the system 400, a reduced-diameter inlet orifice 150 and an air-tight seal 402 between the FAIMS cell 155 and the mass spectrometer 157 combine to enable the mass spectrometer vacuum system to pull a rate-restricted, pressure-reduced flow of gas through the FAIMS cell. The pressure within the FAIMS cell may thus be maintained at a value between 100-600 torr. The reduced diameter of the inlet orifice (for instance 0.65 mm) has the benefit of reducing the consumption of carrier gas. The reduced flow rate and pressure produce the further beneficial effect of decreased ion residence time within the FAIMS, while not placing undue burden on the mass spectrometer vacuum system and maintaining adequate FAWN separation.

Figure 4B:
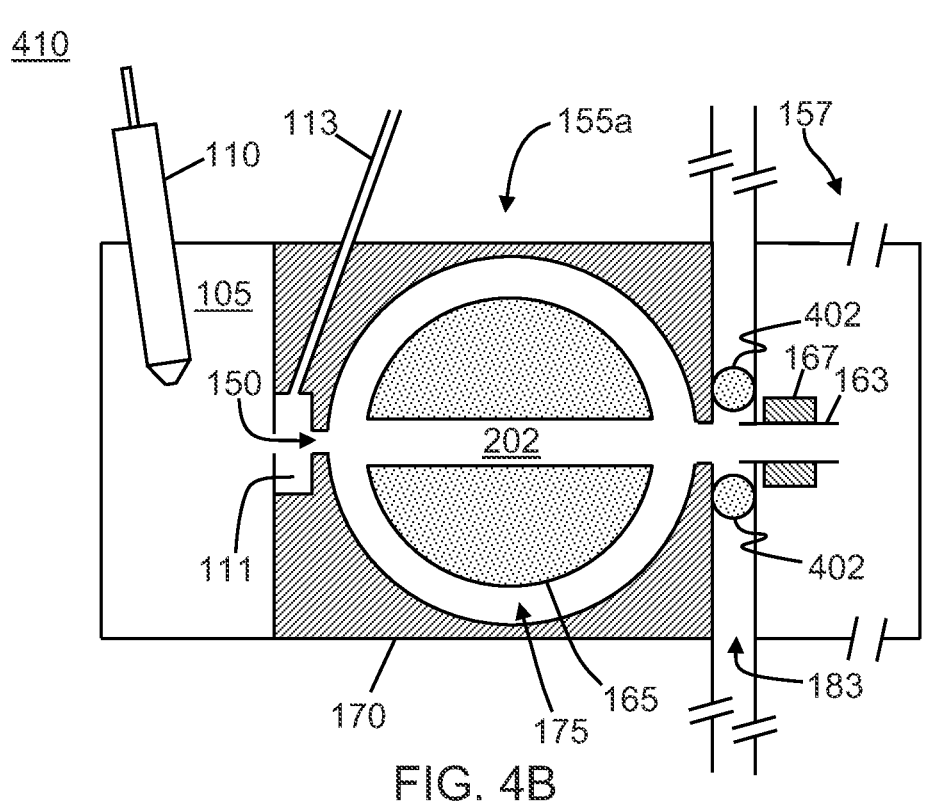
FIG. 4B is a schematic diagram depicting a modification to the system depicted in FIG. 4A, wherein the ion mobility device may be optionally configured either for FAIMS operation or so as to operate as a non-selective ion transport apparatus.

FIG. 4B is a schematic diagram depicting a modification to the system depicted in FIG. 4A. The system 410 shown in FIG. 4B comprises a FAIMS cell 155a (see, for instance, FIGS. 2A, 2B) having a rotatable or displaceable the cylindrical inner electrode 165 that includes a conduit 202 such that the ion FAIMS cell may be configured either for FAIMS operation or so as to operate as a non-selective ion transport apparatus, as previously described. This provides the additional benefit of switching between FAIMS separation and no FAIMS separation without the need to remove or replace the FAIMS cell 155a. Alternatively, the FAIMS cell 155b (see, for instance, FIGS. 2C, 3C) may be employed.

Figure 5A:
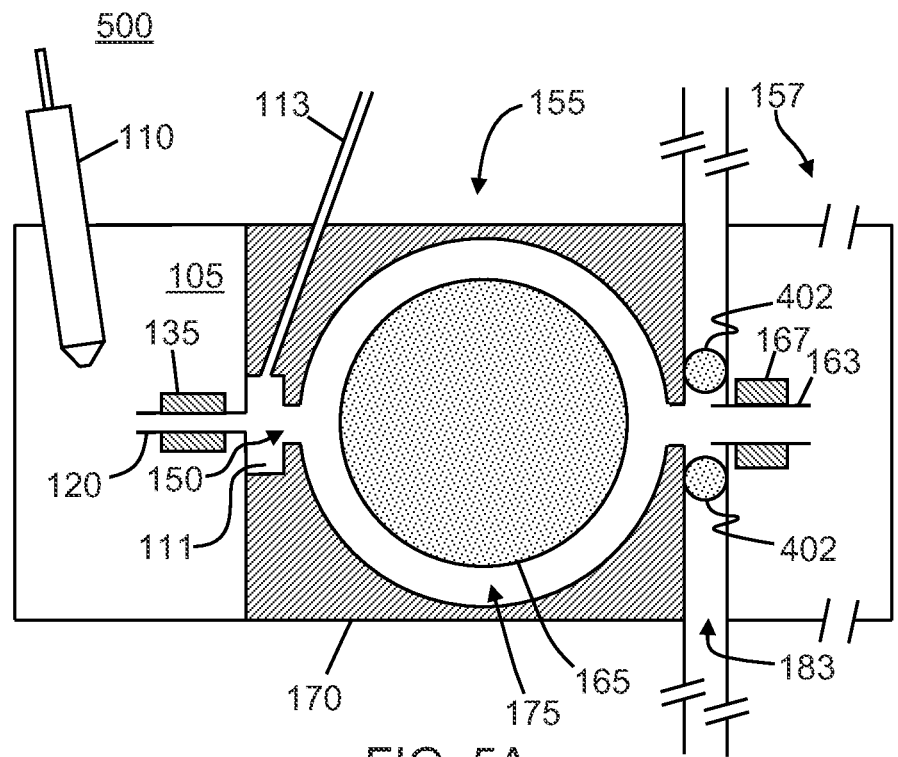
FIG. 5A is a schematic diagram depicting a fourth embodiment of a system for analyzing ions including an ion mobility device in accordance with the present teachings.
Figure 5B:
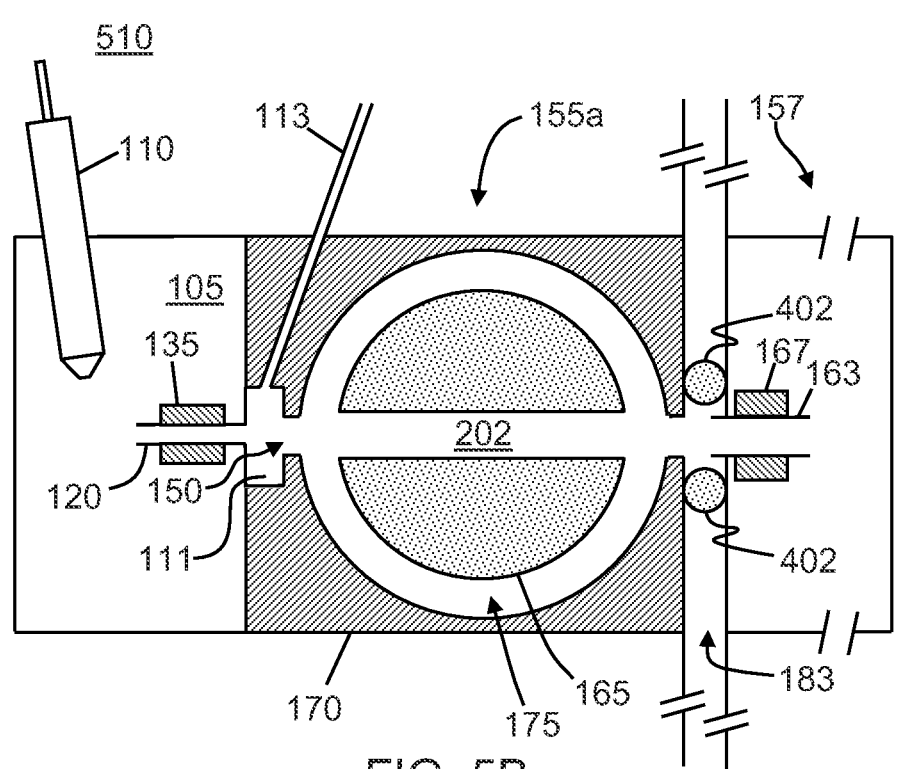
FIG. 5B is a schematic diagram depicting a modification to the system depicted in FIG. 5A, wherein the ion mobility device may be optionally configured either for FAIMS operation or so as to operate as a non-selective ion transport apparatus.

FIG. 5A is a schematic diagram depicting a fourth embodiment of a system for analyzing ions including an ion mobility device in accordance with the present teachings. As in the system 400 (FIG. 4A), the system 500 (FIG. 5A) utilizes the vacuum system of the mass spectrometer 157 to maintain a reduced pressure within the FAIMS cell 155. In the system 500, the restriction of the rate of flow of carrier gas is provided by ion transfer tube 120, such as a capillary tube, that it coupled to the desolvation chamber 111 and the inlet orifice 150 of the FAIMS cell 155. A heater jacket 135 may be coupled to the ion transfer tube so as to promote de-solvation and solvent evaporation prior to ions entering the FAIMS cell. The system 510 shown in FIG. 5B is modified relative to the system 500 by replacement of the FAIMS cell 155 with the reconfigurable FAIMS cell 155*a* (or, alternatively, with the reconfigurable FAIMS cell 155*b*).

Figure 6A:
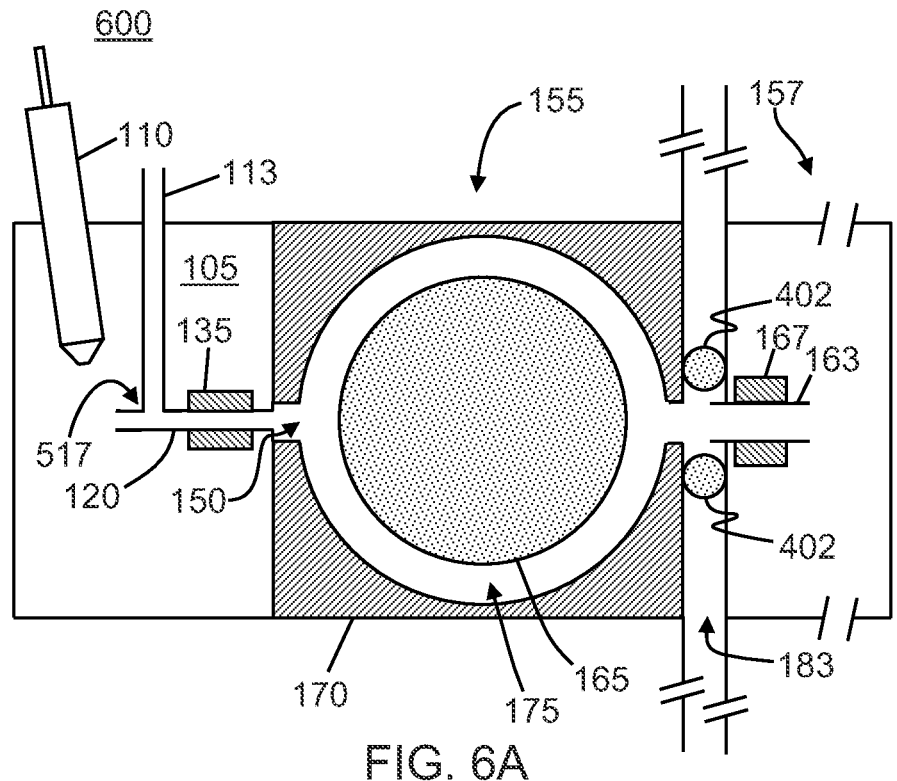
FIG. 6A is a schematic diagram depicting a fifth embodiment of a system for analyzing ions including an ion mobility device in accordance with the present teachings.
Figure 6B:
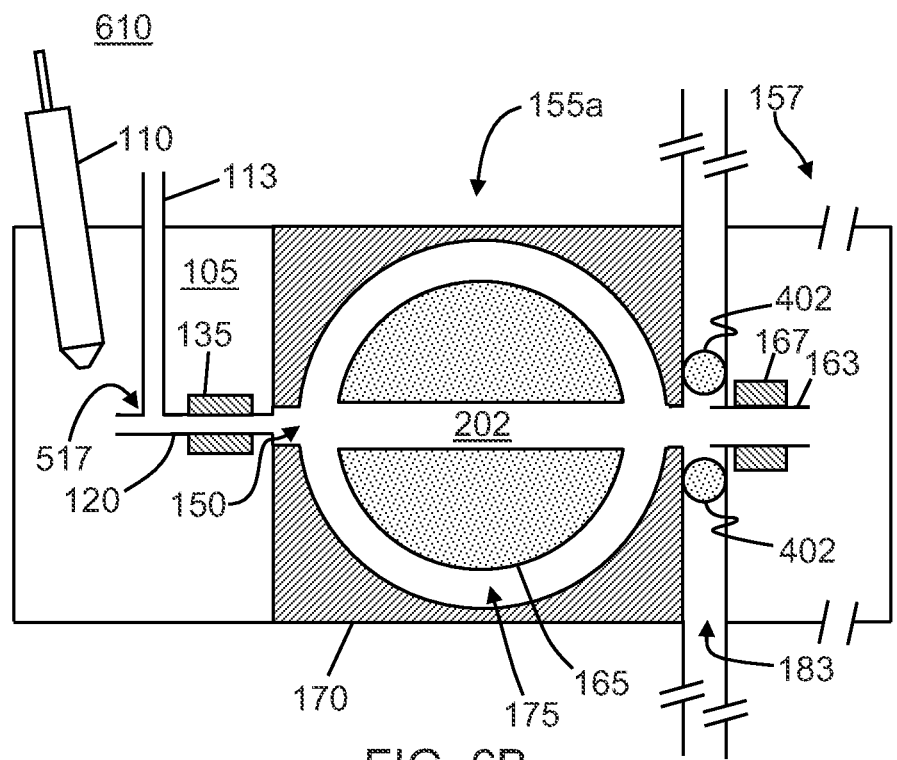
FIG. 6B is a schematic diagram depicting a modification to the system depicted in FIG. 6A, wherein the ion mobility device may be optionally configured either for FAIMS operation or so as to operate as a non-selective ion transport apparatus.

FIG. 6A is a schematic diagram depicting another embodiment of a system for analyzing ions including an ion mobility device in accordance with the present teachings. The system 600 depicted in FIG. 6A is similar to the system 500 depicted in FIG. 5A except that, in the system 600, the carrier gas delivery conduit 113 is moved so as to join with and provide carrier gas to the ion transfer tube 120 at a junction 517 upstream from the heater jacket 135. This arrangement facilitates droplet desolvation within the heated ion transfer tube 120 prior to entry of sample into the inlet orifice 150 thereby eliminating the need for a desolvation chamber (e.g., component 111 in FIG. 3C) near the inlet orifice. The system 610 shown in FIG. 6B provides a modification in which the FAIMS cell 155 is replaced by the reconfigurable FAIMS cell 155*a* (or, alternatively, with the reconfigurable FAIMS cell 155*b*).

Figure 7A:
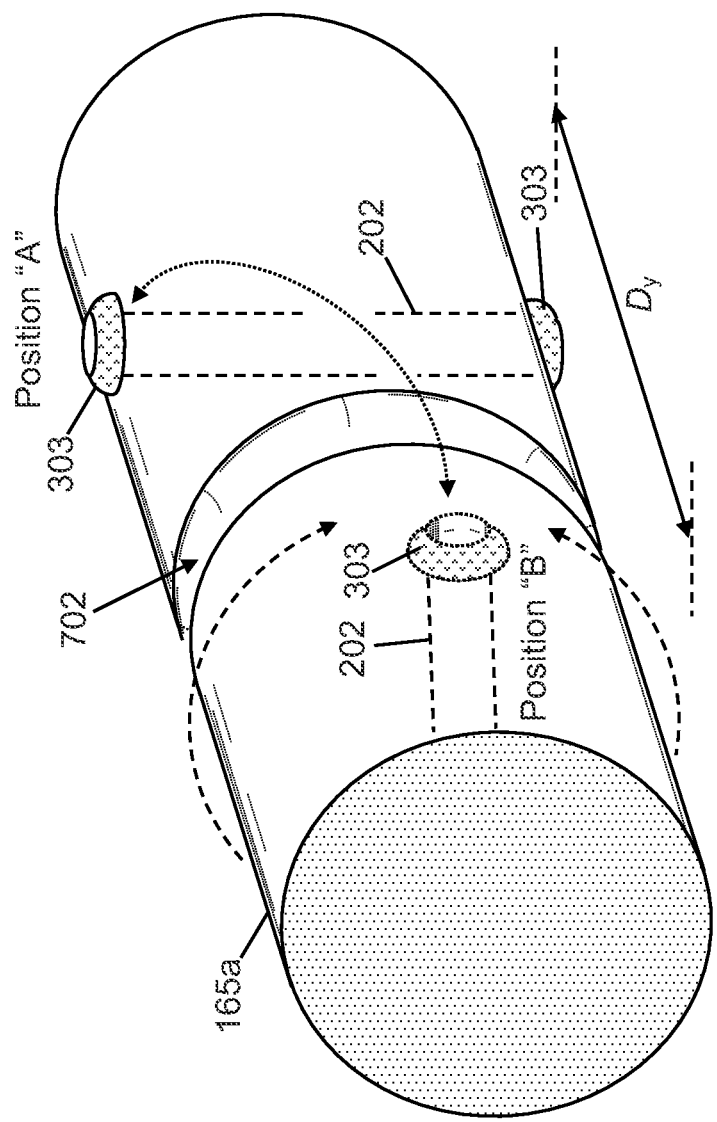
FIG. 7A is a schematic illustration of a first reconfigurable central FAIMS electrode having an ion transfer channel passing therethrough, in accordance with the present teachings.
Figure 7B:
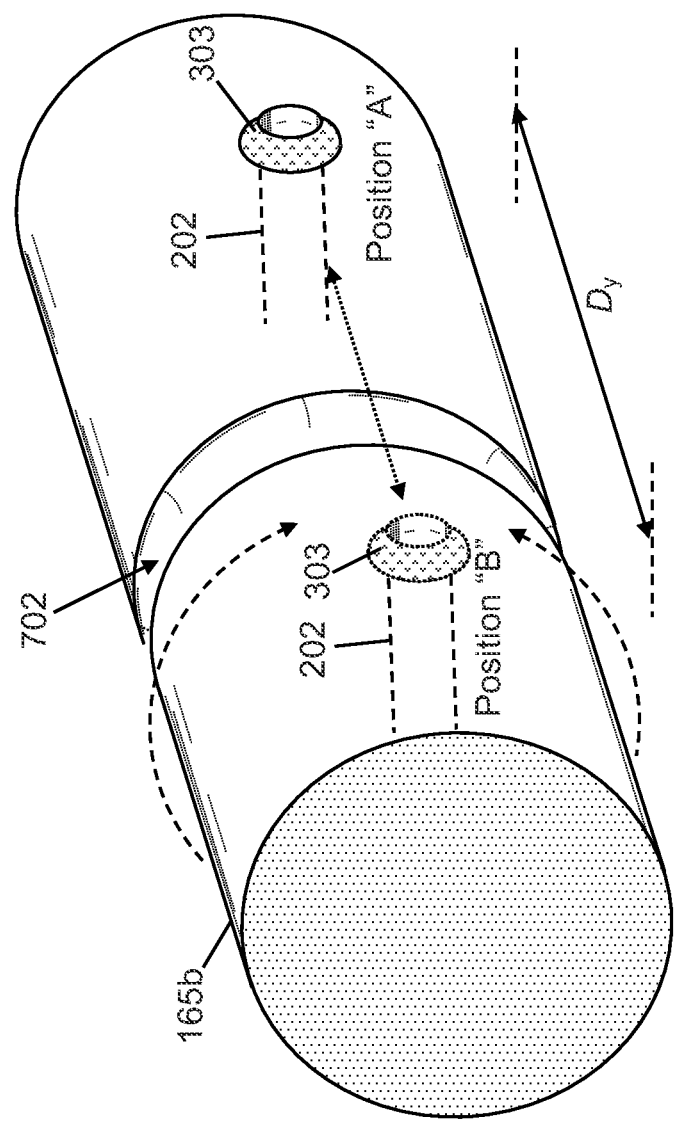
FIG. 7B is a schematic illustration of an alternative reconfigurable central FAIMS electrode having an ion transfer channel passing therethrough, in accordance with the present teachings.

FIGS. 7A-7B are schematic perspective illustrations of two alternative reconfigurable central FAIMS electrodes, each having an ion transfer channel passing therethrough, accordance with the present teachings. The respective FAIMS inner electrode is depicted, in perspective view, as a portion of a cylinder, in each of FIGS. 7A-7B. The FAIMS inner electrode 165*a* illustrated in FIG. 7A comprises a single conduit 202 and optional bushings or gaskets 303 surrounding the conduit 202. The electrode 165*a* may be rotated from a first position, position "A", to a second position, position "B", and back again as indicated by the double-headed dotted arrow. In the position "B" the ends of the conduit 202 align with the inlet orifice 150 and the outlet orifice 185 of the outer electrode (not shown in FIG. 4). Thus, position "A" corresponds to FAIMS operation, as depicted in FIG. 2A and FIG. 3A, whereas position "B" corresponds to ion transfer operation (with FAIMS disabled), as depicted in FIGS. 2B, 2C, 3B and 3C.

In the example shown in FIG. 7A, the movement between the two positions corresponds to a spiral motion, as may readily be accomplished by mounting the inner electrode 165*a* on a threaded spindle portion (not shown) that passes through a threaded bore in a stationary portion of an associated FAIMS apparatus. However, it is also possible to employ a simple rotational motion about the axis of the cylinder, without lateral movement of the conduit 202 parallel to the axis of the cylinder. Such latter configuration, including a simple rotation without lateral motion, is within the scope of the invention. However, such a configuration may place the conduit apertures and any bushings or gaskets in the flow path of carrier gas and entrained ions when the apparatus is in its operable FAIMS configuration (e.g., as in FIG. 2A and FIG. 3A), a disposition which may, in some instances, lead to sub-optimal operation. Thus, the spiral or screw-like motion shown in FIG. 7A is expected to be advantageous, in most instances.

As discussed previously herein, the disposition of the conduit 202, in position "A", at an angle that is substantially perpendicular to a hypothetical line connecting the inlet orifice 150 to the outlet orifice 185 (see, for instance, FIG. 2A) substantially hinders or prevents flow of gas and ions through the conduit 202 during FAIMS operation. This flow through the conduit 202 is further impeded during FAIMS operation by the separation, shown as $D_y$, in FIGS. 7A, 7B, parallel to the axis of the cylindrical electrode 165*a*, between position "A" and the zone of most ion flow between the inlet orifice 150 and the outlet orifice 185 (these inlet and outlet orifices not shown in FIGS. 7A-7B). The central portion of such flow zone is indicated by dashed arrows in FIG. 7A; these arrows represent gas and ion flow within a plane that is perpendicular to the axis of electrode 165*a* and that includes the center lines of the inlet and outlet orifices (i.e., the plane of the drawings in FIGS. 2A-2C and FIGS. 3A-3C). The gaskets or bushings 303 may serve to essentially prevent flow through the conduit 202 in position "A" (FAIMS operation) and to constrain flow to substantially only through the conduit 202 in position "B" (ion transfer operation).

The ion transfer tube 165*a* may further comprise a circumferential feature or perturbation of the cylindrical surface, such as groove 702, so as to confine ion flow around the cylindrical electrode to a region near dashed arrows when the apparatus is in a configuration for FAIMS operation when the conduit is in position "A"). Such surface features are described in greater detail in United States Patent Application Publication No. 2008/0067366 in the name of inventor Belford and assigned to the assignee of the instant application. As discussed in Belford, the groove may be replaced by a ridge, or else a groove or ridge may be provided in the enclosing outer FAIMS electrode (not shown) or else grooves or ridges may be provided in both inner and outer FAIMS electrodes. Such features may perturb the electric fields surrounding the inner electrode in a fashion so as to confine ions within a desired zone. Only one such groove 702 is illustrated in FIG. 7A, but a second groove or feature may also be disposed on the electrode on the opposite side of the position "B" from the illustrated groove, so as to provide ion confinement along both axial directions.

FIG. 7B illustrates another inner electrode 165*b* in accordance with the present teachings. The electrode 165*b* shown in FIG. 7B is similar to the electrode 165*a* of FIG. 7A, except that the displacement between position "A" and position "B" is only laterally, parallel to the axis of the cylindrical electrode, without rotation. A circumferential feature or perturbation of the cylindrical surface, such as groove 702 may serve to prevent ions from passing through the conduit 202 in position "A", even though the conduit 202 remains parallel to a hypothetical line between the center of the inlet orifice 150 and the center of the outlet orifice 185. The two electrodes 165*a*, 165*b* shown in FIG. 4 are two non-limiting examples of electrodes that may be used in systems comprising a FAIMS apparatus coupled to a mass spectrometer in accordance with the present teachings.

Figure 8:
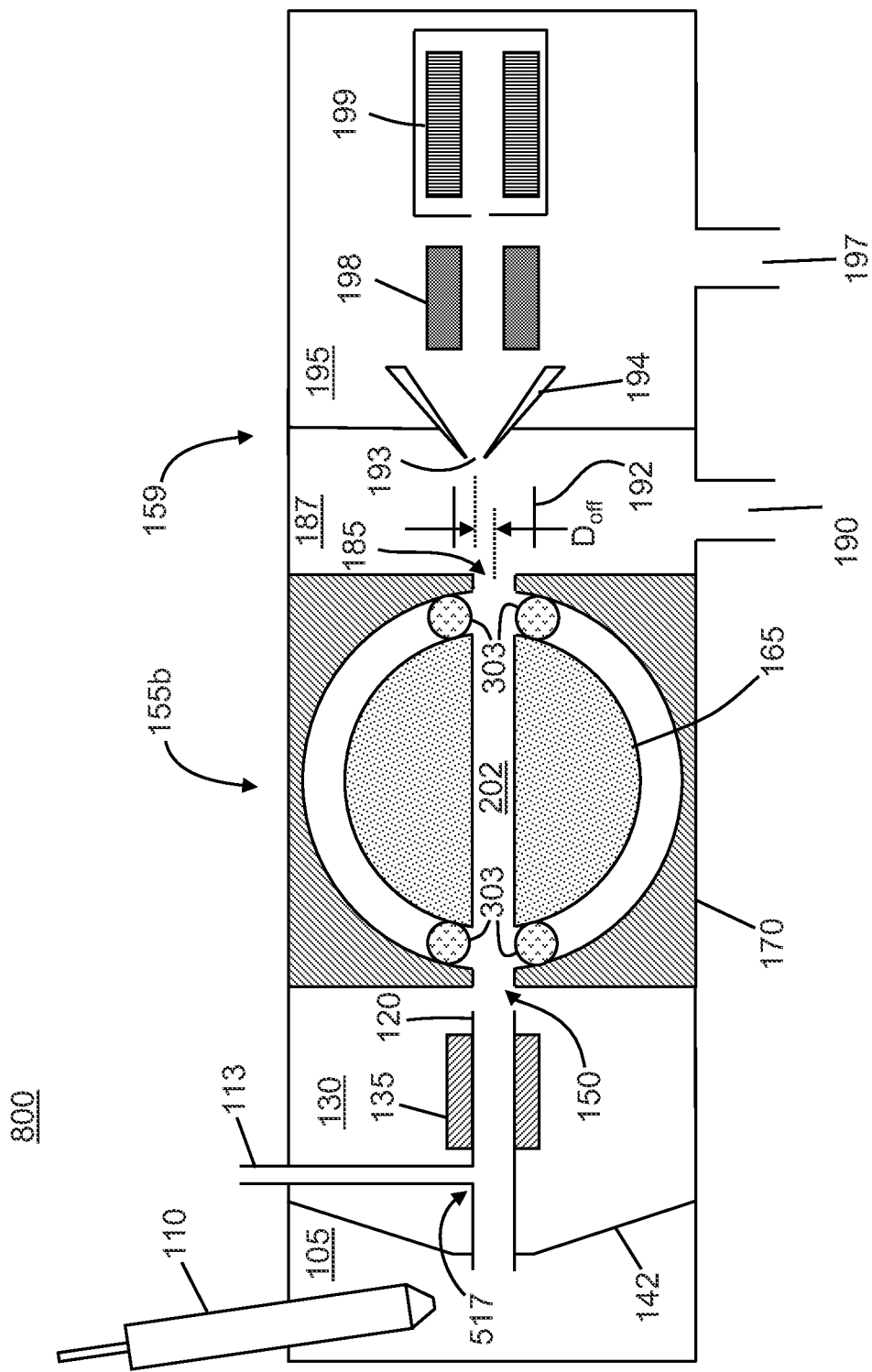
FIG. 8 is a schematic illustration depicting a sixth embodiment of a system for analyzing ions including an ion mobility device in accordance with the present teachings, configured for FAIMS operation.

FIG. 8 is a schematic illustration depicting another embodiment of a system for analyzing ions including an ion mobility device in accordance with the present teachings, configured for FAIMS operation. The system 800 illustrated in FIG. 8 is similar to the system 340 shown in FIG. 3C, except that the carrier gas delivery conduit 113 is moved so as to join with and provide carrier gas to the ion transfer tube 120 at a junction 517 upstream from the heater jacket 135. This arrangement facilitates droplet desolvation within the heated ion transfer tube 120 prior to entry of sample into the inlet orifice 150 thereby eliminating the need for a desolvation chamber (e.g., component 111 in FIG. 3C) near the inlet orifice.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. As but one example, although FAIMS apparatuses having displaceable or rotatable cylindrical electrodes have been described, it should be apparent that it is possible to employ rotatable spherical or ovoid inner FAIMS electrodes having internal conduits or bores with similar effects. Thus, neither the description nor the terminology is intended to limit the scope of the invention. Any publications, patents or patent application publications mentioned in this specification are explicitly incorporated by reference in their respective entirety.

What is claimed is:

1. A system for analyzing ions, comprising:
    an ion source for generating ions;
    a High Field Asymmetric Waveform Ion Mobility Spectrometry (FAIMS) cell comprising:
        (a) a gas inlet;
        (b) an outer electrode having a generally concave inner surface and comprising:
            (i) an ion inlet operable to receive the ions from the ion source and a carrier gas from the gas inlet; and
            (ii) an ion outlet; and
        (c) an inner electrode having a conduit therethrough and having a generally convex outer surface that is disposed in a spaced-apart and facing arrangement relative to the inner surface of the outer electrode so as to define at least one annular ion separation region therebetween; and
    a mass analyzer for mass analyzing ions transmitted by the FAIMS cell through the ion outlet,
    wherein the inner electrode is moveable between a first position and a second position, the first position facilitating movement of the ions through the at least one annular ion separation region, the second position facilitating movement of the ions through the conduit.

2. A system for analyzing ions as recited in claim 1, further comprising a gap between the FAIMS cell and the mass analyzer for atmospheric pressure exhaust of the carrier gas.

3. A system for analyzing ions as recited in claim 1, further comprising:
    a housing of the mass analyzer comprising at least one evacuated chamber;
    a gas-tight coupling between the FAIMS cell and the at least one evacuated chamber; and
    at least one vacuum port coupled to the at least one evacuated chamber for maintaining the at least one evacuated chamber and the ion separation region at sub-atmospheric pressure.

4. A system for analyzing ions as recited in claim 3, wherein the sub-atmospheric pressure is within the range 100-600 ton.

5. A system for analyzing ions as recited in claim 1, further comprising:
    an ion transfer tube for transporting the ions from the ion source to the ion inlet; and
    a heater coupled to the ion transfer tube for heating the ion transfer tube.

6. A system for analyzing ions as recited in claim 1, wherein a movement of the inner electrode between the first and second positions is such that a point on the generally convex outer surface of the inner electrode undergoes a displacement parallel to an axis of the inner electrode.

7. A system for analyzing ions as recited in claim 1, wherein the generally convex outer surface of the inner electrode comprises at least one circumferential surface feature that partially inhibits migration of ions in parallel to an axis of the inner electrode within the ion separation region.

8. A system for analyzing ions as recited in claim 1, further comprising at least one gasket or bushing that seals an aperture of the conduit of the inner electrode to either the ion inlet or the ion outlet when the inner electrode is disposed in the second position.

9. A system for analyzing ions, comprising:
    an ionization chamber;
    an atmospheric pressure ion source within the ionization chamber for generating ions;
    a first reduced pressure chamber;
    an ion transfer tube having a first end disposed within the ionization chamber for receiving ions from the ion source and a second end disposed within the first reduced pressure chamber;
    a heater in thermal contact with the ion transfer tube applying heat to the ion transfer tube;
    a carrier gas conduit for introducing a flow of carrier gas into the ion transfer tube;
    a High Field Asymmetric Waveform Ion Mobility Spectrometry (FAIMS) cell within the first reduced pressure chamber comprising:
        (a) an outer electrode having a generally concave inner surface and comprising:
            (i) an ion inlet operable to receive the ions and the carrier gas from the second end of the ion transfer tube; and
            (ii) an ion outlet; and
        (b) an inner electrode having a conduit therethrough and having a generally convex outer surface that is disposed in a spaced-apart and facing arrangement relative to the inner surface of the outer electrode so as to define at least one annular ion separation region therebetween, the inner electrode being moveable between a first position and a second position, the first position facilitating movement of the ions through the at least one annular ion separation region, the second position facilitating movement of the ions through the conduit;
    a mass analyzer for mass analyzing ions transmitted by the FAIMS cell through the ion outlet; and
    a housing of the mass analyzer comprising at least one evacuated chamber fluidically coupled to the ion outlet of the FAIMS cell.

10. A system for analyzing ions, comprising:
    an ion source for generating ions;
    a High Field Asymmetric Waveform Ion Mobility Spectrometry (FAIMS) cell comprising:
        (a) a gas inlet;
        (b) an outer electrode having a generally concave inner surface and comprising:
            (i) an ion inlet operable to receive the ions from the ion source and a carrier gas from the gas inlet; and
            (ii) an ion outlet; and
        (c) an inner electrode having a conduit therethrough and a generally convex outer surface that is disposed in a spaced-apart and facing arrangement relative to the inner surface of the outer electrode so as to define at least one annular ion separation region therebetween, the inner electrode being moveable between a first position and a second position, the first position facilitating movement of the ions through the at least one annular ion separation region, the second position facilitating movement of the ions through the conduit;
a mass analyzer for mass analyzing ions transmitted by the FAIMS cell through the ion outlet, the mass analyzer separated from the FAIMS cell by a gap therebetween;
a gas-tight coupling between the FAIMS cell and the mass analyzer within the gap; and
at least one vacuum port coupled to the mass analyzer for maintaining the mass analyzer and the FAIMS ion separation region at sub-atmospheric pressure.

11. A system for analyzing ions as recited in claim 10, wherein the sub-atmospheric pressure is within the range 100-600 torr.

* * * * *